United States Patent
Kietzmann et al.

(10) Patent No.: US 6,599,479 B1
(45) Date of Patent: Jul. 29, 2003

(54) DEVICE AND PROCEDURE FOR THE ELECTRICALLY TRIGGERED MICRODROP RELEASE WITH A DISPENSING HEAD

(75) Inventors: Markus Kietzmann, Wolfratshausen (DE); Markus Kalkum, New York, NY (US); Thomas Przewieslik, Berlin (DE); Holger Eickhoff, Berlin (DE); Carsten Arold, Berlin (DE)

(73) Assignee: Max-Planck-Gesellschaft zur Forderung der Wissenschaften e.V. (DE)

( * ) Notice: Subject to any disclaimer, the term of this patent is extended or adjusted under 35 U.S.C. 154(b) by 55 days.

(21) Appl. No.: 09/586,199

(22) Filed: Jun. 2, 2000

Related U.S. Application Data

(63) Continuation of application No. PCT/EP98/07893, filed on Dec. 4, 1998.

(30) Foreign Application Priority Data

Dec. 5, 1997 (DE) .......................... 197 54 000

(51) Int. Cl.[7] .............. B01L 3/02; B01L 3/00; G01N 1/10; G01N 1/00
(52) U.S. Cl. .............. 422/100; 422/99; 436/180; 73/863.32; 73/864; 73/864.01; 73/864.11; 73/864.25; 73/864.31; 73/DIG. 4
(58) Field of Search ........... 422/99, 100; 73/863.32, 73/864, 864.01, 864.11, 864.25, 864.31, DIG. 4; 436/180

(56) References Cited

U.S. PATENT DOCUMENTS

| | | | | |
|---|---|---|---|---|
| 3,568,735 A | * | 3/1971 | Lancaster | |
| 4,367,478 A | | 1/1983 | Larsson | |
| 4,399,712 A | * | 8/1983 | Oshikubo et al. | |
| 5,045,286 A | * | 9/1991 | Kitajima et al. | |
| 5,053,100 A | * | 10/1991 | Hayes et al. | |
| 5,223,226 A | * | 6/1993 | Wittmer et al. | |
| 5,273,905 A | * | 12/1993 | Muller et al. | |
| 5,306,510 A | * | 4/1994 | Meltzer | |
| 5,658,802 A | | 8/1997 | Hayes et al. | |
| 5,681,757 A | | 10/1997 | Hayes | |
| 5,916,524 A | * | 6/1999 | Tisone | |
| 5,927,547 A | * | 7/1999 | Papen et al. | |
| 6,063,339 A | * | 5/2000 | Tisone et al. | |
| 6,203,759 B1 | * | 3/2001 | Pelc et al. | |
| 6,232,129 B1 | * | 5/2001 | Wiktor | |
| 6,296,811 B1 | * | 10/2001 | Sasaki | |
| 6,309,891 B1 | * | 10/2001 | Shalon et al. | |
| 2001/0005489 A1 | * | 6/2001 | Roach et al. | |
| 2001/0008615 A1 | * | 7/2001 | Little et al. | |
| 2001/0014477 A1 | * | 8/2001 | Pelc et al. | |
| 2001/0055814 A1 | * | 12/2001 | Saski | |
| 2002/0001544 A1 | * | 1/2002 | Hess et al. | |

FOREIGN PATENT DOCUMENTS

| | | |
|---|---|---|
| EP | 08219956 | 8/1996 |
| EP | 08233710 | 9/1996 |
| EP | 0810438 | 9/1998 |
| WO | WO 97/48818 | 12/1997 |

\* cited by examiner

*Primary Examiner*—Jill Warden
*Assistant Examiner*—Brian R Gordon
(74) *Attorney, Agent, or Firm*—Piper Rudnick LLP

(57) ABSTRACT

A multi-channel dispensing head including a plurality of micropipettes, each micropipette having an electrically actuatable trigger device with a ground and signal terminal; and a shared carrier having a plurality of receptacles located in a one- or two-dimensional arrangement and sized and shaped to receive said micropipettes, each receptacle having a ground and signal contact, wherein the ground and signal contacts on the carrier are spaced apart in the direction of a longitudinal axis extending through the respective micropipettes and each of the ground and signal contacts on the carrier contacting the ground and signal terminals of the trigger devices, respectively.

12 Claims, 10 Drawing Sheets

FIG. 12
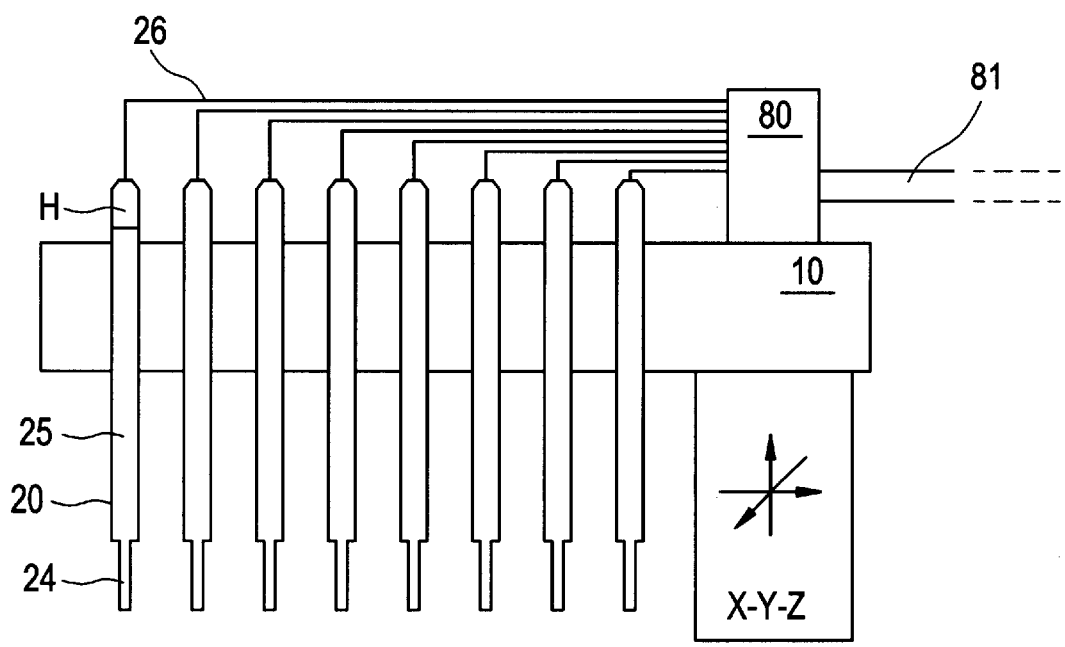
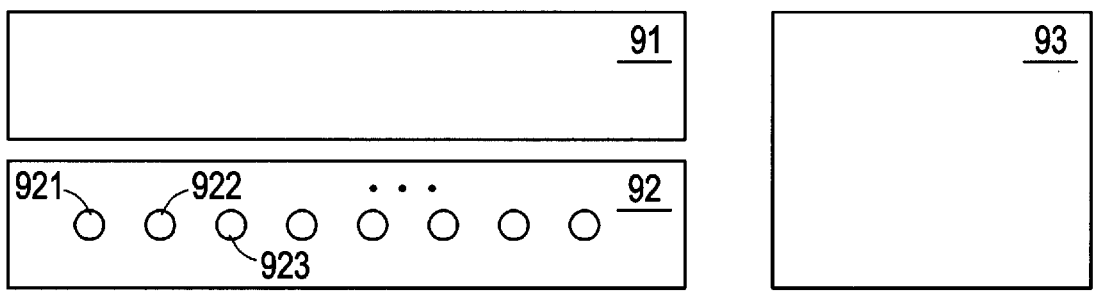

US 6,599,479 B1

DEVICE AND PROCEDURE FOR THE ELECTRICALLY TRIGGERED MICRODROP RELEASE WITH A DISPENSING HEAD

RELATED APPLICATION

This is a continuation of International Application No. PCT/EP98/07893, with an international filing date of Dec. 4, 1998, which is based on German Patent Application No. 197 54 000.7, filed Dec. 5, 1997.

FIELD OF THE INVENTION

The invention relates to a dispensing head set up for the time-controlled, electrically triggered release of microdrops, in particular, to a multi-channel dispensing head with separately triggerable micropipettes, and a procedure for using such a dispensing head.

BACKGROUND

Dispensing heads or modules are widely used for tasks in biotechnology or chemical technology for the controlled release of small volumes of liquid in the form of microdrops. One example of this is the fabrication of miniaturized DNA arrays for genetic engineering applications, wherein a small drop size yields a high cloning density, for which piezoelectrically activated micropipettes are particularly well suited. DNA clones, microorganisms, cells, cell constituents or biomolecules are normally stored as active substances in microtiter plates with numerous recesses (e.g., 96 or 384). Rapidly fabricating arrays consisting often thousand different DNA sequences, for example, requires dispensing modules that can convey liquids from microtiter plates to substrate surfaces for combination purposes in a highly parallel manner or at a sufficient serial rate.

It is generally known that single-channel dispensing heads or multi-channel dispensing heads can be used in the form of a linear sequential arrangement of micropipettes. These conventional dispensing systems exhibit the following disadvantages.

When using a single-channel dispensing head with a single micropipette, the substances to be combined must be conveyed from a reservoir (e.g., microtiter plate) to a reaction substrate, wherein a cleaning step is required during each substance change. This procedure is unacceptable for practical applications in combinatory biotechnology or chemistry because it is time-intensive.

While multi-channel dispensing heads, which essentially consist of a series of 8 to 16 single-channel dispensing heads, do make it possible to reduce the time outlay due to the parallel operation of individual micropipettes, the mounting and control equipment they require is still expensive. Since every individual micropipette is equipped with two control lines for activating the piezo element, and a liquid line for applying a rinsing or charging pressure, conventional multi-channel dispensing heads are complex and cumbersome arrangements.

For example, in the case of a dispensing head with a series of 8 electrically activated micropipettes, a total of 16 control lines and 8 pressure lines would have to be incorporated, all connected with corresponding individual control and pressure devices. If such a multi-channel dispensing head is to be passed over a substrate with an x-y-z positioning device, the complex design of the dispensing head constitutes a crucial disadvantage for the accuracy of dispensing head positioning due to the weight and required inclusion of numerous individual lines. However, imprecise microdrop placement limits the effectiveness of conventional dispensing systems in an unacceptable manner.

Another disadvantage lies in the relatively high susceptibility of the sequentially arranged single-channel micropipettes to failure. Finally, each of the sequentially attached single-channel dispensing heads requires so much space that the micropipette tips have greater distances than the conventional modular dimensions of microtiter plates. This makes a substance absorption by microtiter plates ineffective.

Thus, it would be advantageous to provide an improved multi-channel dispensing head distinguished, in particular, by a simplified design, simplified controllability, reduced reaction time and elevated positioning accuracy. It would also be advantageous to provide improved applications for such a dispensing head.

SUMMARY OF THE INVENTION

The basic idea of the invention is to provide a multi-channel dispensing head in which micropipettes are arranged on a shared carrier in a two-dimensional or planar manner each with an electrically actuatable trigger device, which has a ground and signal terminal, the carrier having a ground or signal contact for each ground and signal terminal, wherein the ground and signal contacts on the carrier are arranged in two planes separated and electrically insulated from each other. The contacts on the carrier are spaced apart relative to the axial expansion (or longitudinal expansion) of the micropipettes. This configuration enables a greatly simplified design with a more compact micropipette arrangement.

The invention can be realized with many kinds of micropipettes that are equipped with an electrically actuatable trigger device and set up to release a microdrop after a pressure pulse is triggered in the volume of the micropipette. The trigger device can be a piezo device, a valve arrangement (in combination with a pressure line) or any corresponding electrical pressure device. The two-dimensional or planar arrangement of micropipettes on a shared carrier can encompass any regular or irregular arrangement. However, a regular arrangement with straight or concentric rows is preferred.

In a rectangular matrix arrangement, the micropipettes form rows and columns aligned at a right angle to each other. In an oblique-angled matrix arrangement, the micropipettes form straight rows and columns that are aligned obliquely (not perpendicular) to each other. In a circular arrangement, the micropipettes form concentric circles. In the latter case, the rows and columns mentioned below are formed by radially arranged (straight) micropipette rows and circular micropipette rows.

In a first embodiment, the dispensing head according to the invention includes one or more micropipette rows on a shared carrier, wherein the ground contacts of each series are electrically interconnected, and the signal contacts are separately actuatable with a signal demultiplexer circuit.

In a second embodiment, the dispensing head according to the invention includes one or more micropipette rows on a shared carrier, wherein the signal contacts of all rows are electrically interconnected, and the ground contacts are separately actuatable with a demultiplexer circuit.

In a third embodiment, the dispensing head according to the invention includes numerous micropipette series in which the micropipettes are two-dimensionally allocated in columns and rows in the form of a matrix. In this embodiment, the ground contacts of each series are electrically connected, wherein, a ground demultiplexer circuit is provided, with which the shared ground contacts of the individual micropipette rows are separately actuatable. In addition, the signal contacts of each micropipette column are electrically interconnected, wherein the signal demultiplexer circuit is provided to make the combined signal contracts of the micropipette columns separately actuatable.

The demultiplexing technology makes it possible to actuate precisely one trigger device of a micropipette whose position corresponds to the selected row or column by applying the ground or signal potential to one of the rows or columns.

The subject of the invention is also a micropipette with an electrically actuatable trigger device, which has a ground and signal terminal, and exhibits two attachment devices. Each of the attachment devices performs a dual function. First, an attachment device is provided on a carrier or mount to establish an electrical connection between the ground or signal terminal and corresponding electrical control terminals. Second, the attachment devices themselves act as a mechanical coupler or attachment means to secure the micropipette to the carrier or mount. The attachment devices provide a mechanically secure link between the micropipette and carrier or mount, and encompass soldering tags, spring elements or threaded necks.

In an advantageous configuration of the micropipettes, a pressure line connects each micropipette with a distributing device also secured to the carrier, through which charging or cleaning pressure can be imparted to the micropipettes. The distributing device may be either a multi-valve arrangement or a valve-free branch piece.

The micropipettes exhibit a loading volume to receive the working substance to be released in microdrops, and a carrier volume to receive a carrier liquid. In a preferred procedure of the invention, the dispensing head is charged in such a way that a carrier liquid is first received simultaneously in all carrier volumes of the micropipettes. Specific working substances are then received by each micropipette at a working substance reservoir arrangement comprised of numerous reservoirs, which are each aligned in accordance with the micropipette arrangement at the dispensing head. The trigger device is situated in the area of the carrier volume, so that the microdrop release takes place by actuating the trigger devices and imparting the pressure pulse via the carrier liquid to the respective working substance.

BRIEF DESCRIPTION OF THE DRAWINGS

Additional advantages and details of the invention are contained in the following description to the attached drawings. The drawings shown in.

-continued

Figure 5:
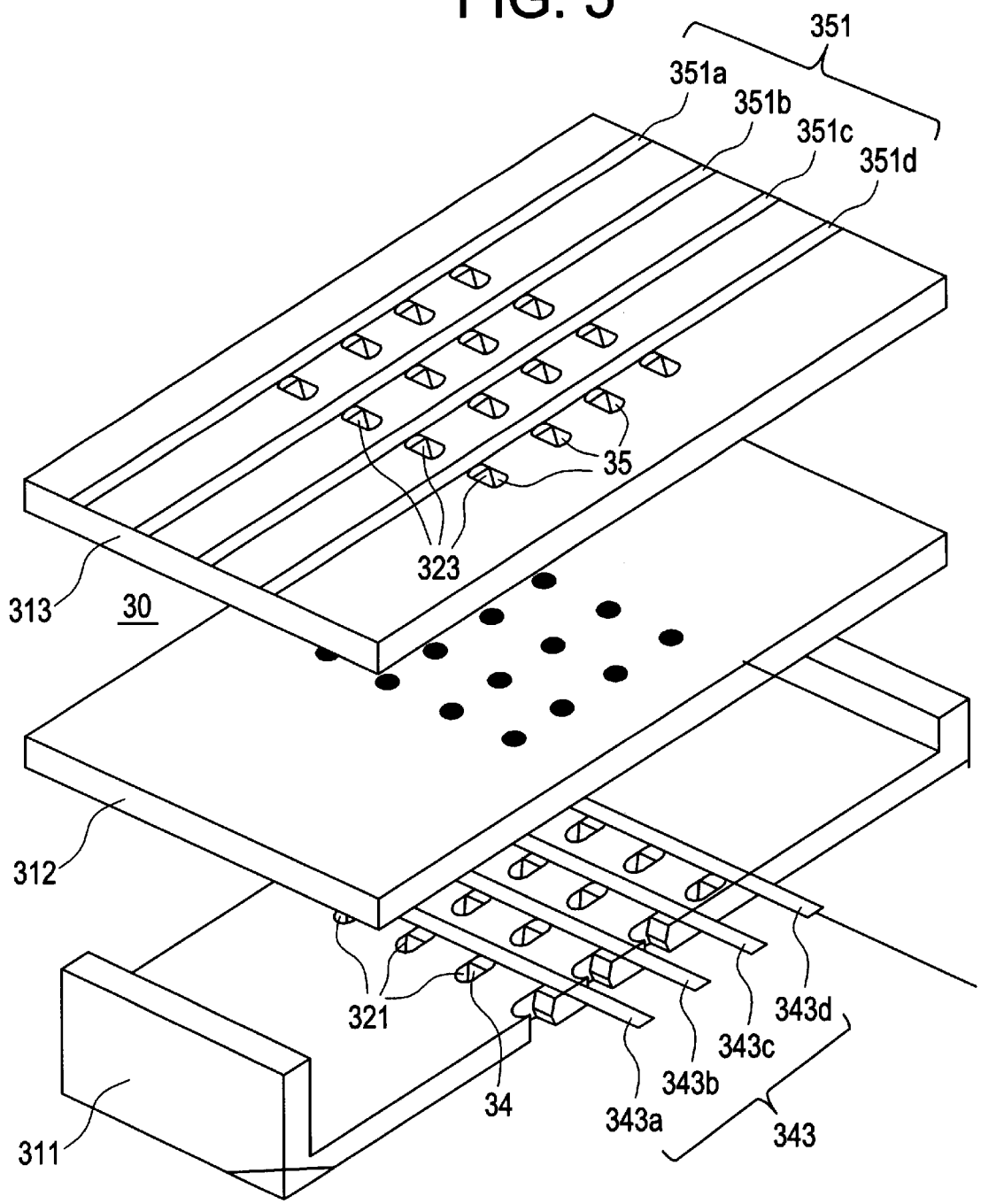
FIG. 5: a schematic perspective view of a carrier of a dispensing head according to a third embodiment of the invention, in which a micropipette matrix is provided.
Figure 6:
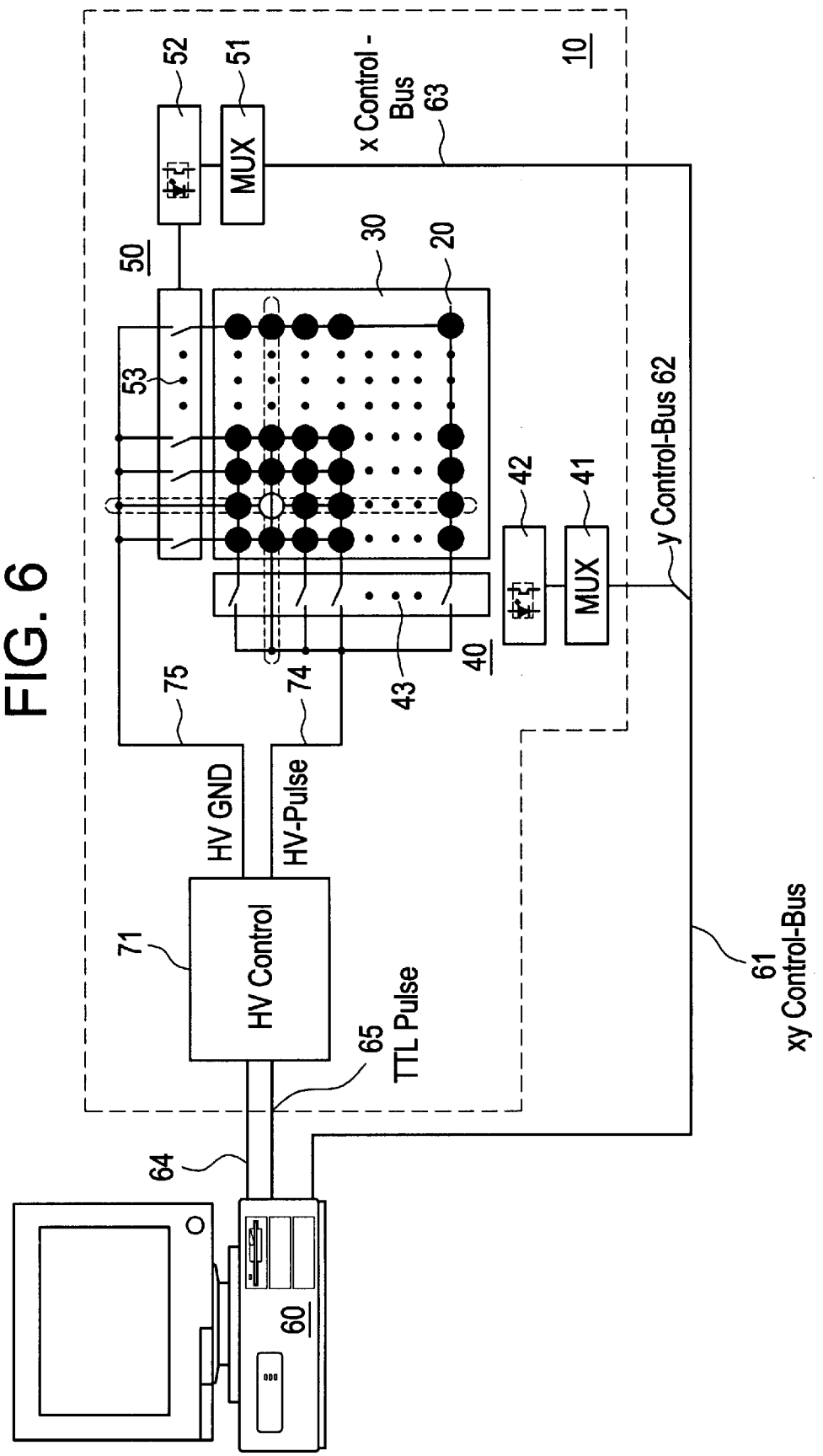
Figure 7:
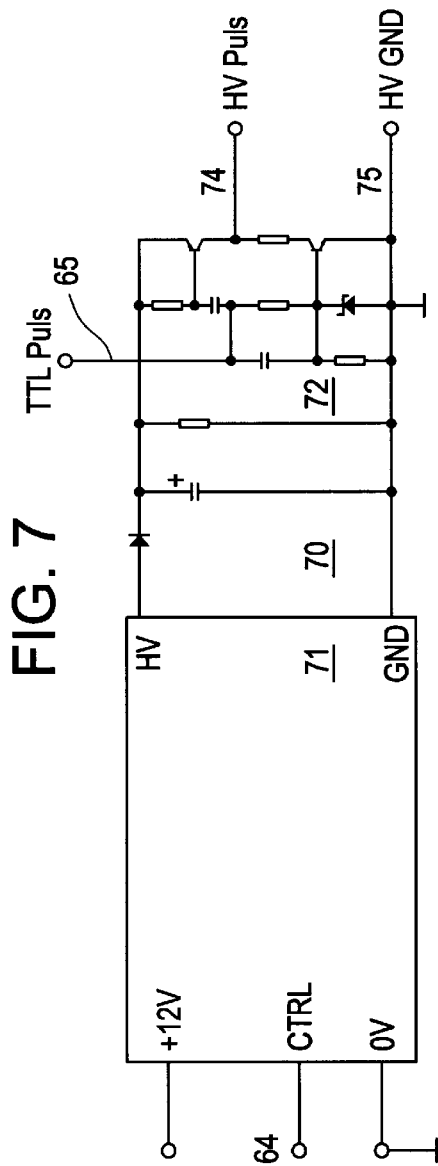
Figure 8:
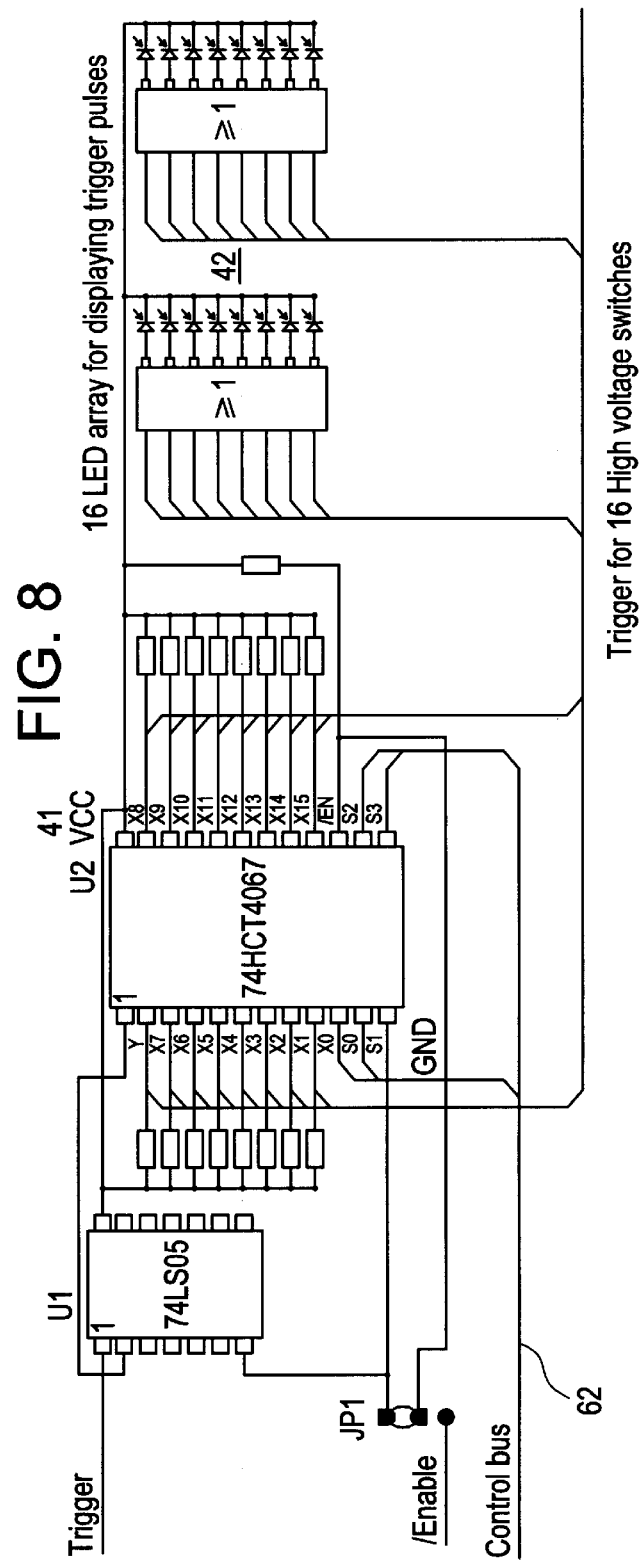
Figure 9:
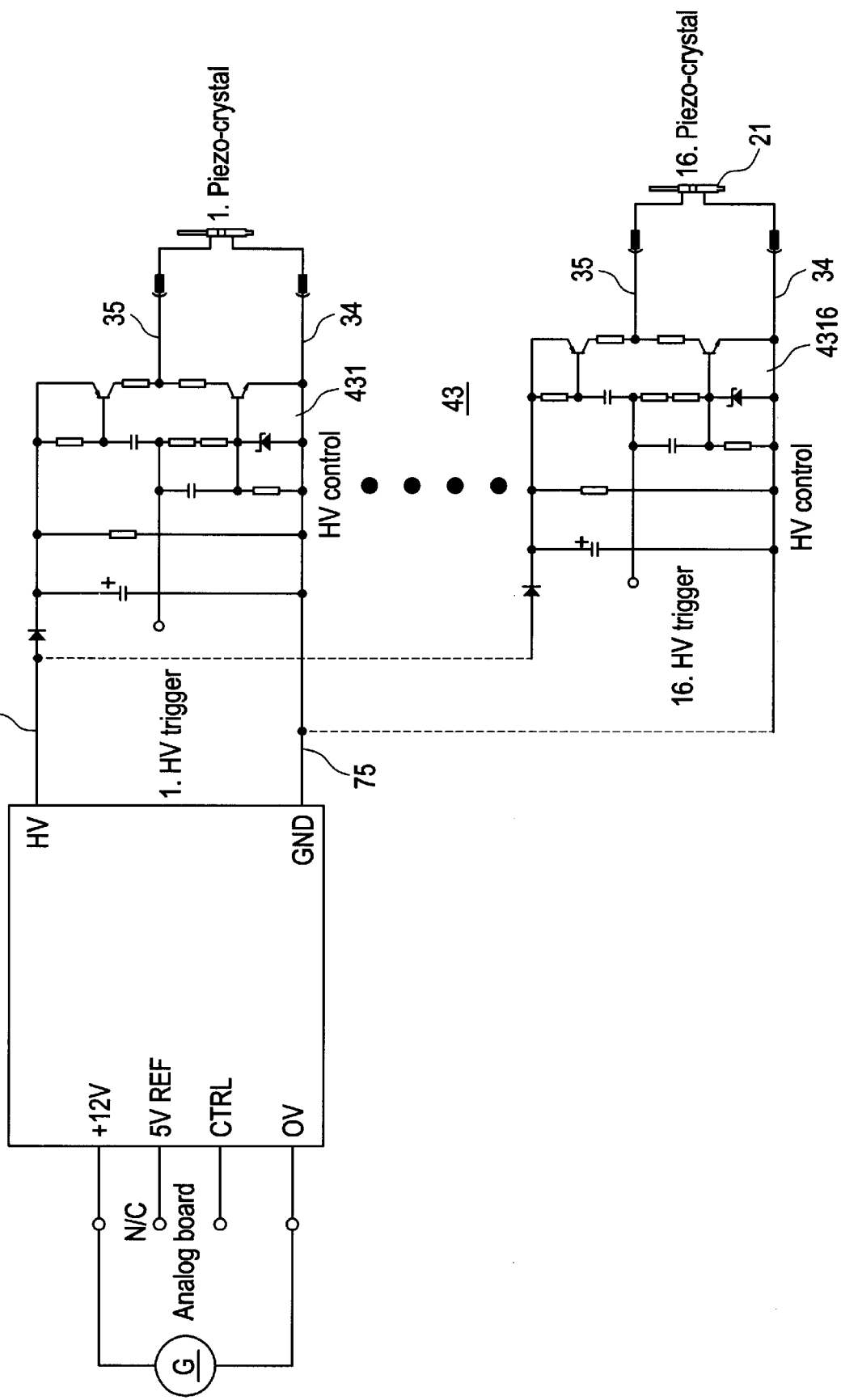
Figure 10:
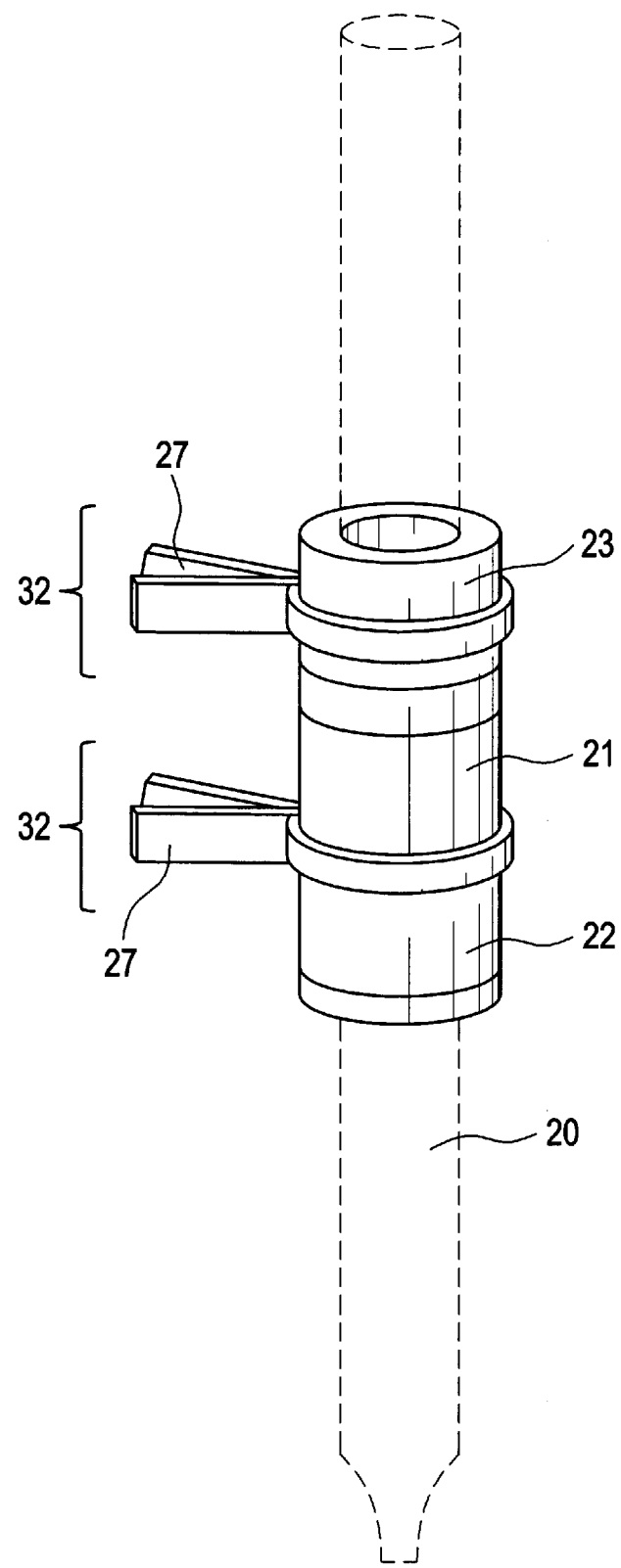
Figure 11:
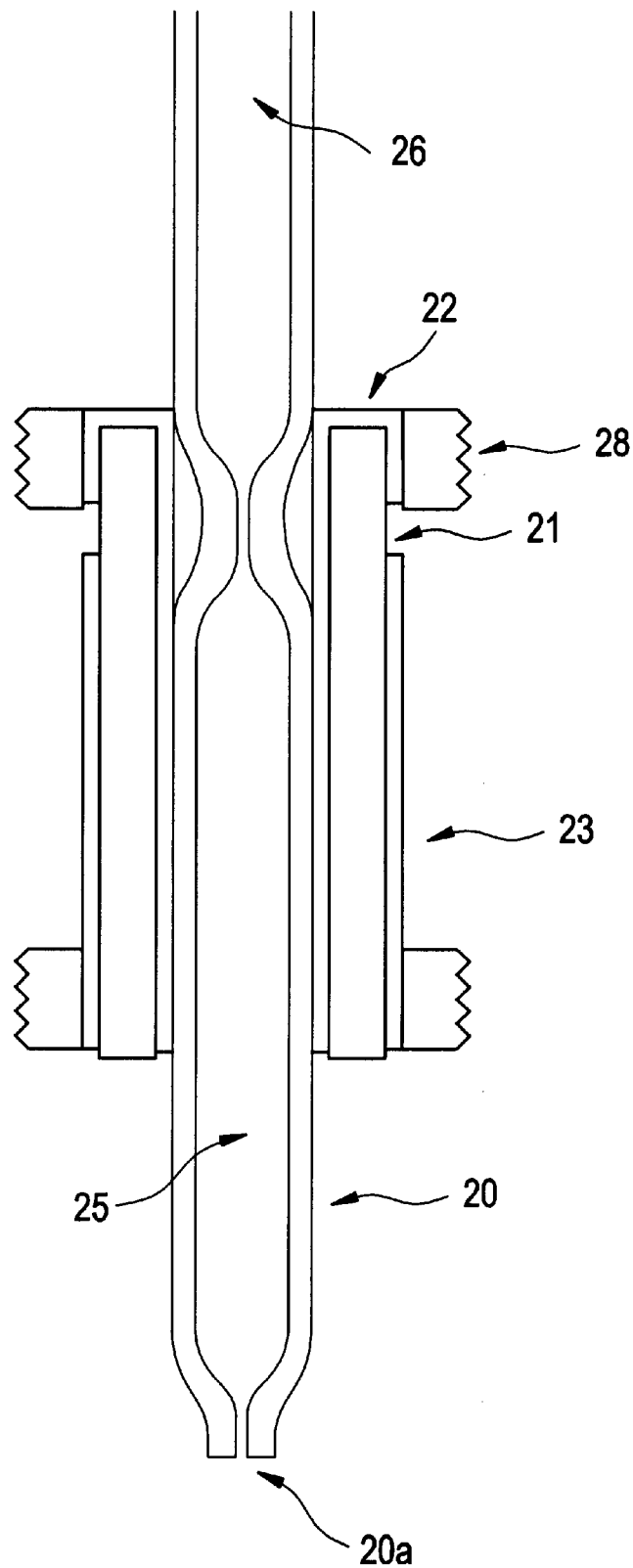

FIG. 6: an overview of the electrical actuation of a multi-channel dispensing head according to FIG. 5;
FIG. 7: a wiring diagram of a high-voltage power supply unit for a multi-channel dispensing head according to FIG. 3 or 5;
FIG. 8: a wiring diagram of a demultiplexer device according to FIG. 5;
FIG. 9: a wiring diagram showing the interaction between the high-voltage power supply unit with the demultiplexer devices according to FIGs. 7 and 8;
FIG. 10: a schematic view of a micropipette modified according to the invention;
FIG. 11: a schematic view of another micropipene modified according to the invention; and
FIG. 12: a schematic overview to explain the use of a multi-channel dispensing head according to the invention.

DETAILED DESCRIPTION OF THE INVENTION

In the following, the invention will be described making reference to a dispensing head with piezoelectrically actuatable micropipettes, which are set up for the vertical release of microdrops on substrates in the sub-$\mu$l range. However, the invention is not limited to this application, but can be generally used in a wide variety of microparticle placement devices with many types of trigger devices in which electrically actuated dispensers are arranged in rows or matrices, and the individual trigger devices of each dispenser are intended to be separately actuatable. In addition, the invention is not limited to the specific format for micropipette arrangement cited by example below, but can be applied at any row length or matrix size for the vertical or horizontal microdrop or particle release. The invention can be implemented with any general or commercially available, electrically actuatable micropipettes, so that micropipette details will not be described below.

Figure 1:
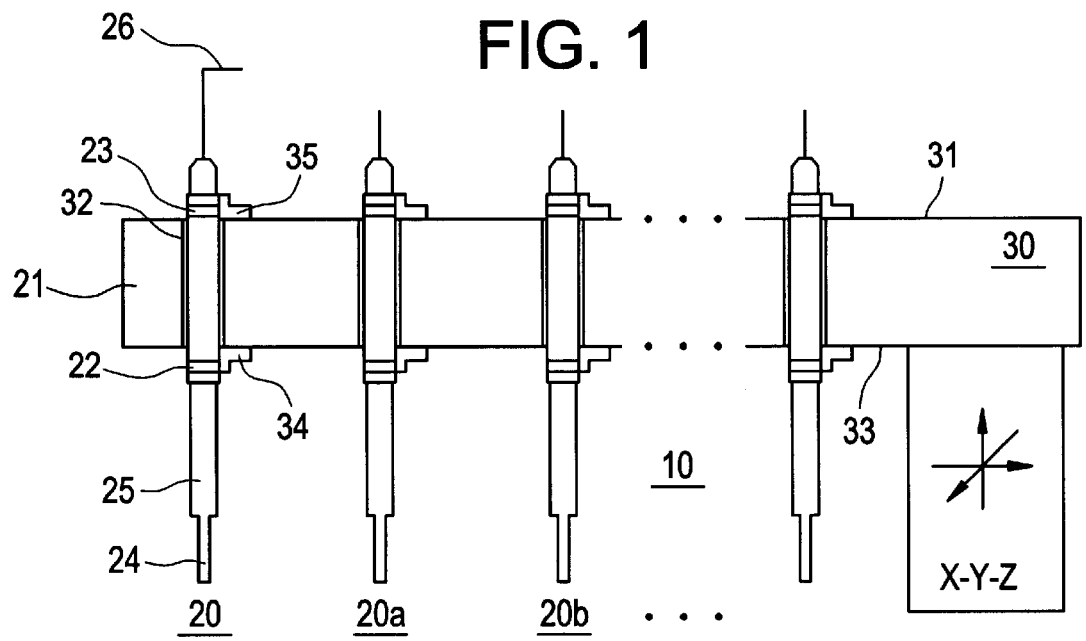
FIG. 1: a schematic partial sectional view of a multi-channel dispensing head according to the invention.

FIG. 1 shows a schematic sectional view of a dispensing head 10 according to the invention with a group of micropipettes 20 (20a,20b, ...) that are attached to a shared carrier 30, which can be adjusted with an x-y-z positioning device. Each micropipette 20 has a piezo element 21 as the trigger device with two control terminals comprising a ground terminal 22 and a signal terminal (or: phase terminal) 23. The micropipette 20 forms a load containing portion 24 at the pipette tip, which goes into a carrier containing portion 25 if needed (see below). The opposite end of the micropipette has a pressure line 26, the details of which are described below.

The carrier 30 consists of at least one plate-shaped carrier element, which has receptacles 32 (32a,32b, ...) for securing the micropipettes 20. In addition, the carrier 30 is provided with contacts 34, 35 at two spaced, electrically isolated, essentially flat areas, which in the depicted example are formed by the surfaces 31, 33 (or side surfaces) of the carrier element, each of these contacts comprising a ground contact 34 and a signal contact 35. The ground and signal contacts 34, 35 are each electrically connected with the ground and signal terminals 22, 23 of the piezo elements 21. Finally, electronic components and devices for attaching and connecting them can be provided on the carrier. To this end, the carrier is preferably a printed circuit board itself. In particular, the complete supply and demultiplexer electronics can be incorporated on the carrier.

An attachment device for holding the micropipette 20 is provided at each receptacle 32 of the carrier element 31. The attachment device is preferably detachable, so that individual micropipettes can be changed out. In a preferred embodiment, the attachment device itself is formed by the ground and signal contacts 34, 35, provided the latter are spring elements, which act to retain the micropipettes 20 with the piezo element 21 in the receptacle 32.

Arranging the micropipettes on the shared carrier makes it possible to reduce the distance between the micropipette tips to such an extent (e.g., 4.5 mm or 9 mm) that a substances can be taken up directly from conventionally used microtiter plates simultaneously for all micropipettes of a dispensing head. In addition, attaching the ground and signal contacts 34, 35 on two separate planes makes it possible to connect contacts in rows or columns without crossing, as will be explained below.

Figure 2:
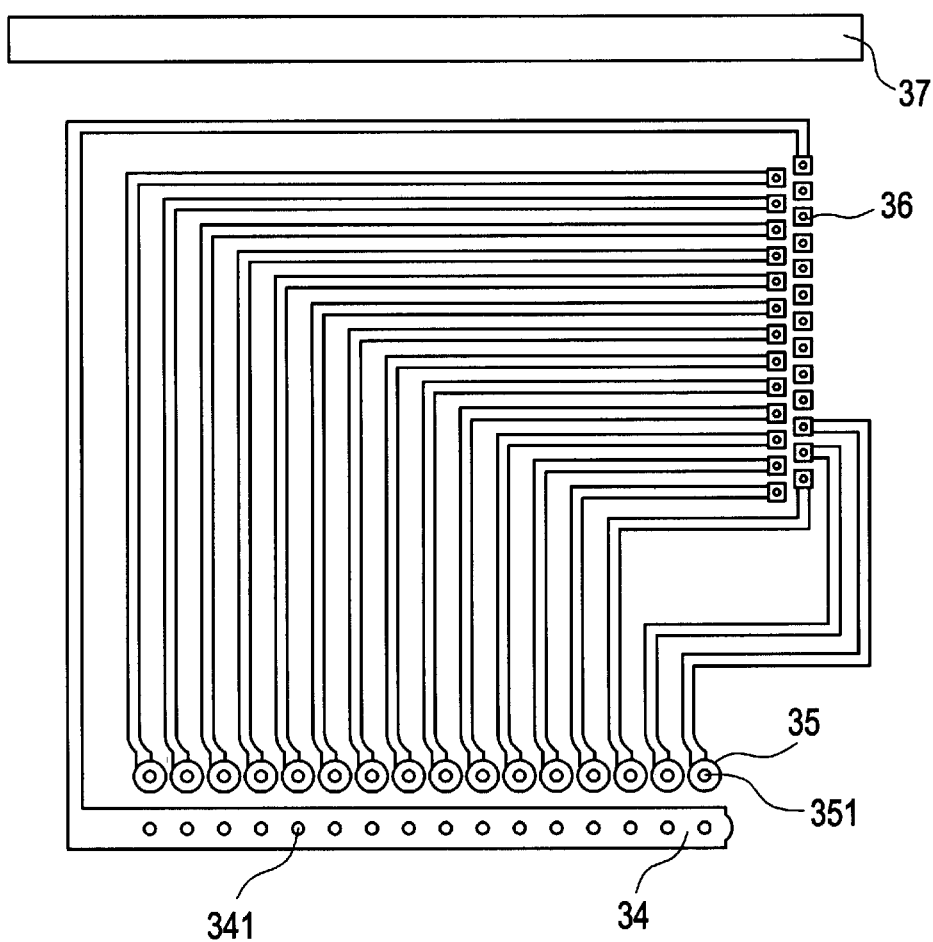
FIG. 2: the contact configuration for a multi-channel dispensing head according to a first embodiment of the invention, in which a micropipette row is provided.

In the first embodiment of the invention, the micropipettes are attached laterally to a shared flat carrier as a linear row. FIG. 2 shows an example for contacting a board (board layout) (not shown), which can be realized as a carrier 30. FIG. 2 shows two contact rows 34, 35, which are provided on the lateral surface of a carrier board and each exhibit numerous through holes 341, 351. These holes are positioned to receive resilient soldering tags, and aligned with corresponding receiving holes on the carrier board (corresponding to the receptacles 32 in FIG. 1). The micropipettes here run parallel to the plane of the carrier.

According to an important feature of the invention, the contacts of one of the contact rows are electrically connected with each other. In the example shown, the ground contacts 34 are connected with each other, while the signal contacts 35 are separate from each other, and individually controllable. A conventional terminal 36 (details not shown) is used to connect the shared ground contact 34 with the ground terminal of a high-voltage power supply device for actuating the piezo elements and the individual control contacts 35 with a phase or signal terminal of the high-voltage power supply device via a demultiplexer circuit.

Figure 3:
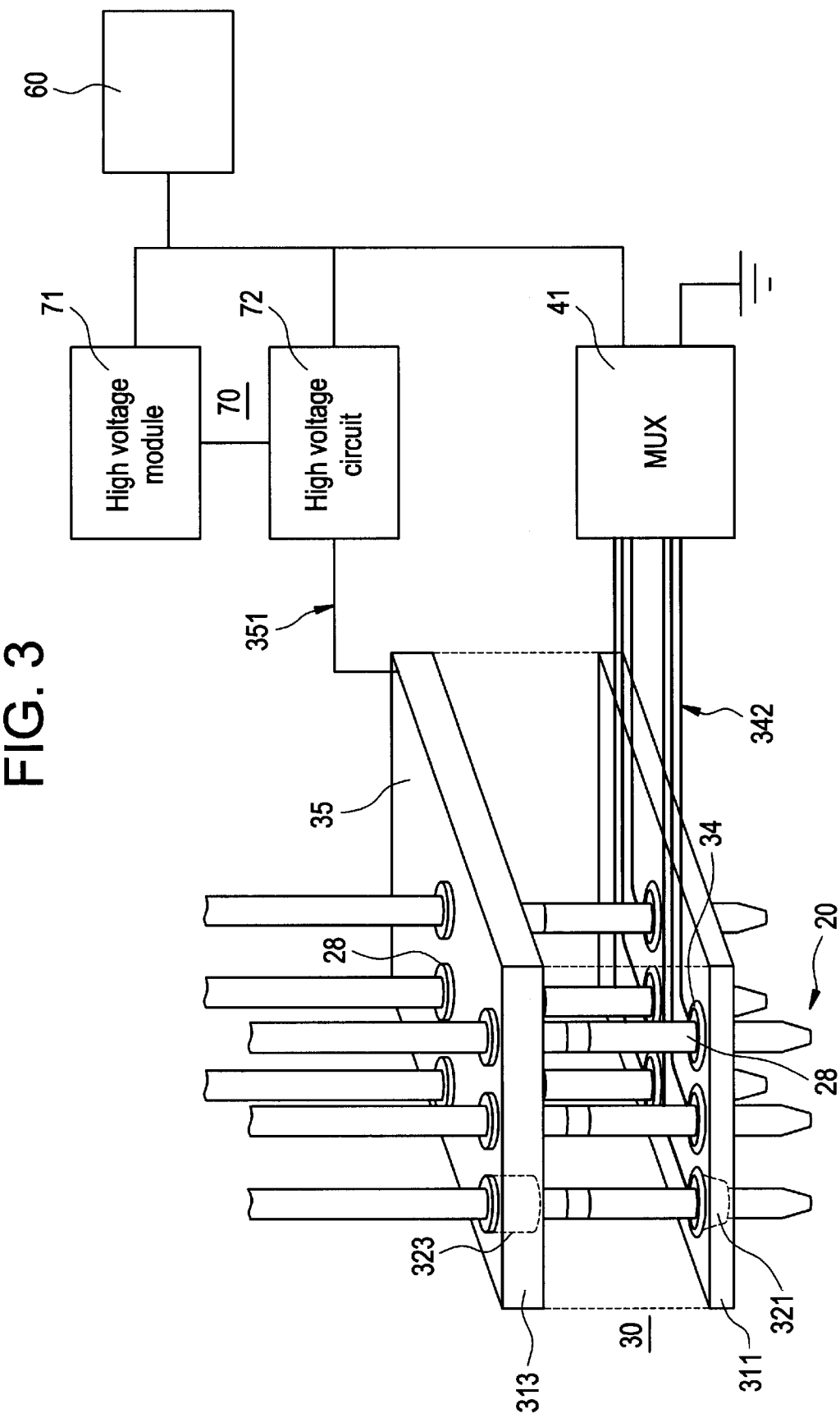
FIG. 3: a schematic overview of the multi-channel dispensing head according to a second embodiment of the invention, in which several micropipette rows are provided.

The reference numeral 37 refers to a mounting device, with which several micropipette rows are interconnected to form a micropipette matrix. This is simplified by the fact that the row arrangement enables a flat layout, so that the micropipettes can be arranged at a small enough distance even in the column direction. The second embodiment of the multi-channel dispensing head according to the invention is shown in FIG. 3. FIG. 3 illustrates the design of a micropipette matrix (section) and its electrical actuation. In the second embodiment, the micropipettes are arranged two-dimensionally as a matrix into several parallel micropipette rows and columns on a shared carrier 30. The example shows only three columns and two rows. However, depending on the application, many more micropipettes are distributed like a matrix. The geometry of the arrangement depends on the application, and preferably corresponds to the geometric arrangement of the reservoirs of a microtiter plate.

The carrier 30 encompasses two carrier part elements comprised of a base plate 311 and a cover plate 313. In addition, a guide plate (not shown) can be provided between the latter, which primarily acts to stabilize the carrier 30, and is shown in a third embodiment according to FIG. 5. Each of the carrier part elements is provided with receptacles 321 and 323, which are aligned toward each other with the carrier part elements combined, and set up to hold one micropipette each. Each of the receptacles 321 or 322 is provided with an inside threaded area, which interacts with a threaded neck of the micropipette (see FIG. 11).

In addition, each receptacle 321 or 323 forms an electrical control terminal for the accompanying micropipette. In the embodiment shown, the cover plate 313 carries a shared signal contact for all micropipettes. The signal contact 35 is formed by an electrically conducting coating (metal plate) of the cover plate 313, and is in contact with the accompanying control system via a connecting cable. The ground contacts 34 are arranged in the plane of the base plate 311 at a distance from the signal contact 35. A signal line 342 leads from the accompanying control system to one of the micropipettes 20.

Figure 4:
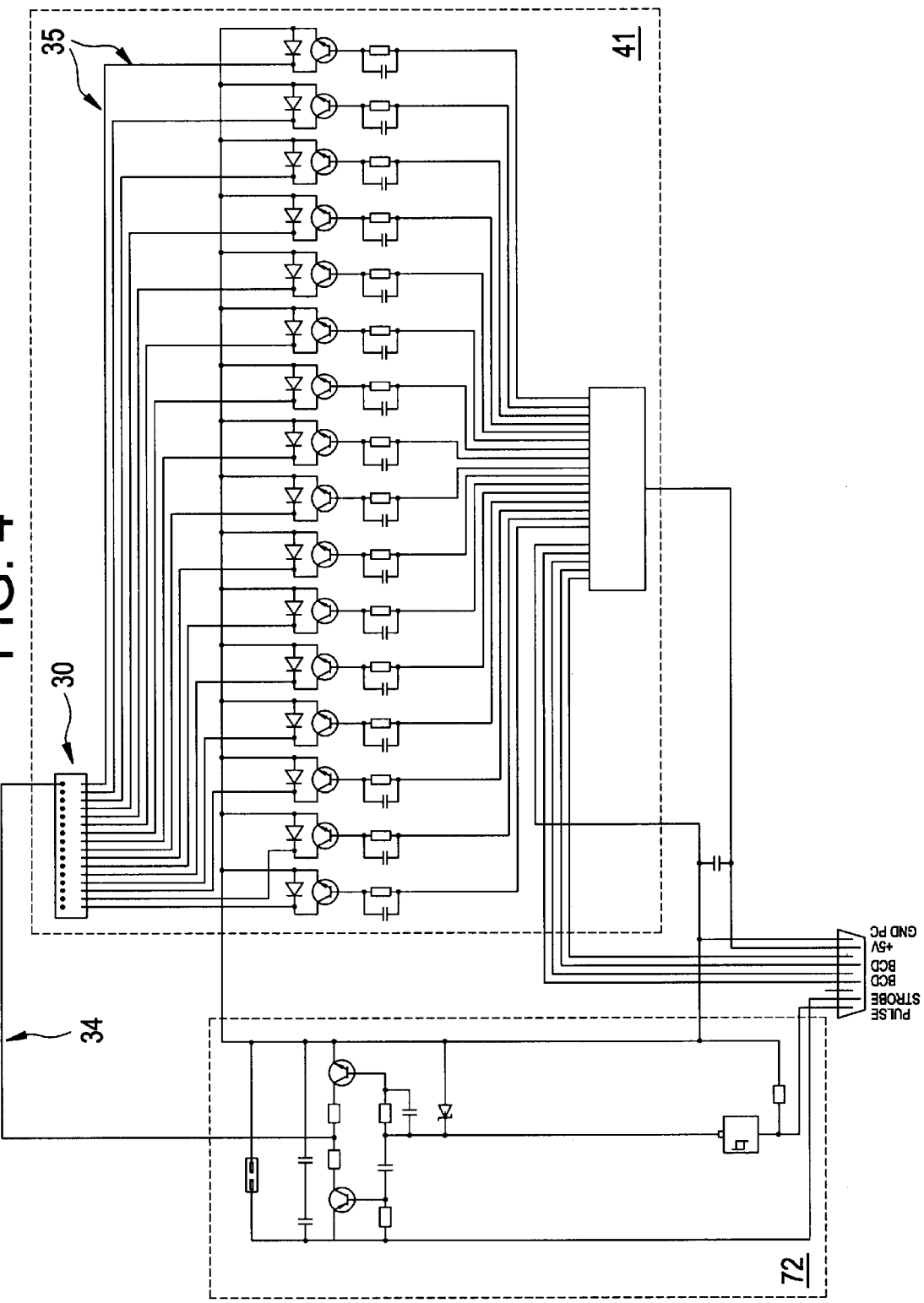
FIG. 4: an overview of the electrical control of the multi-channel dispensing head according to FIG. 3.

In the embodiment according to FIG. 3, the signal contacts of all rows and columns of micropipettes are electrically interconnected, as opposed to which the ground contacts can be individually actuated with a demultiplexer circuit 41. The control system of the multi-channel dispensing head according to FIG. 3 encompasses a power supply unit 70 with a high-voltage source 71 and a controller circuit 72 along with demultiplexer circuit 41, as shown in FIGS. 3 and 4. Both the power supply unit 70 and demultiplexer circuit 41 are connected with a computer-assisted controller (e.g., control computer 60).

The micropipettes 20 can be piezo pipettes, which are each actuated with a voltage pulse of up to about 250 volts.

The pulse amplitude is regulated directly via the power supply unit of the high-voltage source 71. To this end, the control computer 60 (DA card) outputs a voltage value of between about 0 and about 5 volts, which the high-voltage source 71 uses as the control signal. The control voltage excursion of 5 volts corresponds to a high-voltage excursion of 250, for example.

The controller circuit 72 shown in detail in FIG. 4 consists of switching transistors that are activated on the one hand with the set high voltage from the high-voltage source 71 and, on the other, by Schmitt triggers with control pulses from a timer-counter card in the control computer 60. Based on the desired actuation of micropipettes 20, the switching transistors deliver an edge-steep square-wave pulse to the signal contact 35, which is available to all micropipettes simultaneously. The electrical connection with the piezo elements of the micropipettes takes place via the respective threaded necks of the micropipettes.

The demultiplexer circuit 41 shown in detail in FIG. 4 can be a 16-off-4 demultiplexer circuit. The desired micropipettes 20 are selected via a BCD code prescribed by the control computer. The demultiplexer circuit 41 decodes the code, and relays the respective pipette selection to one of many controller circuits, whose number corresponds to the number of micropipettes. The controller circuit activated as a result brings the corresponding ground contact 34 of the desired micropipette 20 to ground potential substantially simultaneously to the high-voltage pulse of the power supply unit 70. This subjects the desired micropipette 20 to a potential difference. The piezo element is then actuated, and liquid is dispensed. The nozzles, whose controller circuits are not activated, remain potential-free, so that the respective micropipettes are also not actuated, and no liquids are dispensed. The electrical connection between the controller circuits of the demultiplexer circuit 41 with the piezo elements of the micropipettes is established via the respective threaded necks (see FIG. 11), and via printed conductors on the base plate 311. Correspondingly, the base plate 311 is preferably a board with etched copper paths.

The advantage to the embodiment according to FIGS. 3 and 4 is that the system can be expanded as desired. Expansion to an increased number of pipettes is possible with minimum technical outlay, since only the one power supply unit 70 is necessary, regardless of the number of pipettes. By contrast, the demultiplexer circuit can be secured to the carrier 30 without any problem, which can in turn be passed over a sample substrate or the like with a mounting device (not shown).

FIG. 5 shows an alternative configuration of a carrier 30 for a matrix-type, two-dimensional micropipette arrangement according to a third embodiment of the invention. The carrier 30 here encompasses three carrier part elements consisting of a base plate 311, a guide plate 312 and a cover plate 313. Each of the carrier part elements is respectively provided with receptacles 321, 322 and 323, which are aligned toward each other with the carrier part elements assembled, and arranged to each hold one micropipette. Each of the receptacles 321 or 323 of the base plate 311 or 313 accommodates an electrical contact 34 or 35, respectively. Hence, the contacts 34 (e.g., ground contacts 34) are arranged in the plane of the base plate 311 at a distance from the contacts 35 (here, signal contacts) in the plane of the cover plate 313. The ground contacts 34 are interconnected in rows by a first contact comb 343. To this end, contact webs 343a, 343b, . . . are provided, which extend along the rows and are connected with each of the contacts 34 located in the respective row. A second contact comb 351 consisting of contact webs 351a, 351b, . . . is provided for the second contact group 35, and connects the contacts by column. "By column" means that the contacts 35 are interconnected in linear columns running perpendicular or diagonal to the linear rows in which the contacts 34 are interconnected. The contact combs 343, 351 are connected with the demultiplexer circuits (not shown), whose function will be described below.

In the embodiment according to FIG. 5, the contacts 34, 35 in turn assume the function of attachment devices. The contacts are each flexibly arranged in the receptacles in such a way that the cross-section of the receptacle is reduced, and a piezo element located in the receptacle is exposed to a mechanical stress. The thickness of the guide plate 312 is selected based on the specific structural shape of the piezo element in such a way that the contacts 34 or 35 each maintain contact with the ground and signal terminals of the piezo elements, which are shown in FIG. 10.

The above-described structure of the multi-channel dispensing head according to FIG. 2 or 5 enables a simplified electronic control through the use of demultiplexer technology. To also simplify handling of the dispensing head by reducing the number of electrical control lines of fixed control and power supply units, a first demultiplexer circuit 40 and/or a second demultiplexer circuit 50 is secured to the dispensing head 10, depending on the embodiment. The demultiplexer circuit 40 is provided for distributing phase or control pulses or signals to the piezo element control, terminals of micropipettes arranged individually or in columns. Correspondingly, the second demultiplexer circuit 50 is provided for distributing ground potentials to the piezo element ground terminals of micropipettes arranged in rows.

FIG. 6 shows a schematic block diagram of the fixed control device 60 (e.g., a computer), the power supply unit 70, which is fixed or movable with the carrier, and the dispensing head 10 (shown with dashed lines) that can be moved relative to the latter with an x-y-z positioning device (not shown). The figure illustrates an important advantage to the invention, namely that, in addition to the two lines 74, 75 for piezo element actuation, only two addition lines 62, 63 are provided for actuating the demultiplexer circuits 40, 50 between the movable dispensing head 10 and the fixed laboratory system.

The control device 60 is used to automatically control the entire microplacement system, in particular, dispensing head positioning and timed microdrop release. To this end, for example, a computer is equipped with an additional timer-counter card, a digital-to-analog converter (e.g., National Instruments PC-A-02DC) and several digital outputs for the control bus lines (e.g., National Instruments PC-DIO-96). The timer-counter card. (e.g., PCL with AM 9513 module) is programmed to generate the piezo pulse length required based on the application (TTL pulses for high-voltage control) and drop frequency. The digital-to-analog converter in control device 60 can be used to vary the output voltage of the high-voltage source 71 of the power supply unit 70. This variation capability is advantageous for adjusting the parameters of the power supply unit 70 to the variables of the micropipettes of the respectively used dispensing head and, if necessary, to the dispensed solutions. The respective variables (pulse voltage, pulse length, drop frequency, etc.) are managed by the control device 60 and stored in databases.

The control device 60 is connected with the demultiplexer circuits 40 and 50 via an x-y control bus 61. In addition, there is a connection with the power supply unit 70 via the voltage adjustment line 64 and the pulse line 65 for the pulse-width and frequency control of the power supply unit 70.

FIG. 7 shows details relating to the power supply unit 70, which consists of a high-voltage source 71 and a controller (pulse shaping) circuit 72. The lines 64 and 65 from the control device 60 are each connected with circuits 71 and 72. A control line 74 and ground line 75 then leads from the power supply unit 70 to the dispensing head 10. A high-voltage pulse is conveyed via the control line 74 as a control signal for the piezo elements of the micropipettes. The high-voltage control unit 71 consists of a commercially available linear voltage amplifier. The controller (pulse shaping) circuit 72 is a quick-switching, edge-precise high-voltage controller circuit, which is controlled by the TTL pulse of the control device 60.

Details of the demultiplexer circuit 40 and its interaction with the control device 60 and the power supply unit 70 are described below making reference to the first embodiment according to FIG. 2 with 16 micropipettes.

In the first embodiment, a group of micropipettes is arranged in a row, wherein all ground contacts 34 of the micropipettes are electrically interconnected. Therefore, a demultiplexer circuit 50 according to FIG. 6 is not provided in this case. However, the details covered below making reference to FIG. 7 and 8 can be applied analogously to the second and third embodiment with micropipettes arranged as a matrix as shown in FIG. 3 or 5. The demultiplexer circuit 50 then has basically the same design and functions as the demultiplexer circuit 40, but in relation to the separate actuation of the ground contacts of interconnected rows.

The demultiplexer circuit 40 (see FIG. 6) comprises a demultiplexer 41, a display device 42 and a switching arrangement 43. The demultiplexer 41 and display device 42 are shown in FIG. 8. The demultiplexer 41 receives a selection signal via the y-control bus 62, which branches from the x-y control bus 61. This signal determines which of the signal contacts 35 of the dispensing head 10 is to be hit by the high-voltage pulse from the power supply unit 70. The demultiplexer 41 can be a type SN74LS4067 digital demultiplexer, for example. The demultiplexer 41 then outputs a trigger signal via one of the 16 demultiplexer output lines 64, which is applied to the display device 42 and switching arrangement 43. The display device 42 is only an aid used to more easily visualize which micropipette of the dispensing head is currently being actuated. The display device 42 is not absolutely necessary for realizing the invention.

The switching arrangement 43, details of which are shown in FIG. 9, acts as a relay group consisting of a number of switching units 431, . . . 4316 corresponding to the number of micropipettes arranged in a row (e.g., 16). Each of the switching units has a transistor switch as the switching means, which responds in response to a trigger signal from one of the sixteen demultiplexer output lines 64, and relays the high-voltage pulse delivered via the signal line 74 to the signal contact 35 of the respectively selected piezo element 21.

Therefore, the trigger signal delivered by the demultiplexer is used to decide which micropipette (or which piezo element) is exposed to the high-voltage pulse. Even though all piezo elements are rigidly connected with the ground potential in the first embodiment, only one micropipette is supplied with power and, hence, made to release microdrops.

In the second embodiment, the second demultiplexer circuit 50 correspondingly encompasses a demultiplexer 51, a display device 52 and a switching arrangement 53. A selection signal is delivered to the demultiplexer 51 via the x-control bus 63 to select which of the micropipette rows connected in relation to the ground contact is to be connected with the ground line 75 from the control device 70. The demultiplexer 51 in turn provides a corresponding trigger signal, in response to which one of the switching units of the switching arrangement 53 switches the ground potential to the corresponding micropipette row. The interaction between the demultiplexer circuits 40 and 50 supplies power to exactly one micropipette corresponding to the row and column currently being exposed to the high-voltage pulse or ground potential. In the example shown in FIG. 5, this is the micropipette in the second column and second row.

The number of switching units 431, . . . 531, . . . in each switching arrangement 43, 53 is adjusted to the respective row and column number of the dispensing head 10. In this way, for example, eight switching units can be provided in switching arrangement 43 and twelve switching units in the switching arrangement 53 given a dispensing head with 96 micropipettes for a microtiter plate with 96 substance reservoirs (reservoir distance roughly 9 mm). The switching units are preferably optically isolated from the demultiplexers to avoid crosstalk between electrical control signals and intensify the demultiplexer signals. To this end, an optical coupler is provided for each switching unit.

A micropipette modified according to the invention is provided with attachment devices that simultaneously provide the electrical and mechanical contact with the carrier. Two embodiments for attachment devices will be described below making reference to FIGS. 10 and 11.

FIG. 10 shows details of a commercially available piezo element 21 with control terminals 22, 23. During application of a control signal (high voltage ranging from roughly 30 to 200 V), the piezo element deforms in such a way that the volume inside the micropipette diminishes, so that a microdrop is released from the tip of the micropipette. In the embodiment according to FIG. 2, each control terminal is connected with the respective contacts in the carrier by a soldering tag 27 that extends into the respective receptacle on the carrier. In the embodiment according to FIG. 5, the soldering tag need not be used, since the contacts 34, 35 in the receptacles 321 or 323 establish direct contact with the control terminals 22, 23.

FIG. 11 shows an alternative pipette configuration. The micropipette 20 consists of a borosilicate glass capillary with an outside diameter of 1 mm and a wall thickness of 41 $\mu$m. The piezo element 21 is a piezoceramic pipe with two control terminals 22, 23, which each encompass an inner electrode and outer electrode (metalized on piezoceramic pipe). The attachment devices are formed by two threaded bushings or necks 28, which each sit at the ends of the piezoceramic pipe. The control terminals 22, 23 are arranged in such a way that one end of the piezoceramic pipe is covered by one of the control terminals. Correspondingly, the threaded necks 28 consist of metallic material in electrical contact with one of the control terminals 22 or 23. The outside periphery of the threaded necks 28 must be provided with a thread corresponding to the inside thread in receptacles 321, 322 on the carrier 30 (see FIG. 3). Other locking means (e.g., latching elements) can be provided in place of the thread.

The threaded necks 28 are bonded to the control terminals by means of an electrically conductive adhesive (e.g., "Circuit Works" from Chemtronics Inc., USA). The axial distance of the control terminals 22, 23 measures roughly 1 cm, and the diameter of the piezoceramic pipe measures roughly 3 mm. The dimensions of the micropipette acting as the dispenser can be tailored to the application.

The micropipette 20 contains a narrowed portion 29 between the carrier volume 25 toward the pipette tip 20a and a reservoir (not shown), which is connected with a pressure line 26 (shown in FIG. 12).

FIG. 12 shows another feature according to the invention, which can simplify handling of a multi-channel dispensing head. As indicated with reference to FIG. 1, each micropipette 20 is provided with a pressure line 26. The pressure lines 26 of all micropipettes are connected with a distributor 80, which is also secured to the dispensing head. A pressure supply line 81 leads from the distributor 80 to a fixed pressure device (not shown). The pressure device is provided to generate underpressures or overpressures for receiving carrier liquids, cleaning or stabilizing the pressure, which are conveyed by the distributor arrangement 80 to the pressure lines 26 (e.g., gas pressure lines).

The distributor 80 can be a multi-valve or a branching arrangement. In the multi-valve arrangement, a number of valves corresponding to the number of micropipettes is provided at the dispensing head., The multi-valve arrangement makes it possible to control the pressure of individual micropipettes for charging or cleaning purposes. In the branching arrangement, the pressure supply line 81 opens into the numerous pressure lines 26 without valves. When using the branching arrangement, the procedure for charging or cleaning, and for receiving substances, is realized as follows. In a first step, the dispensing head is moved to a carrier liquid reservoir 91, so that the micropipette tips are simultaneously immersed in a carrier liquid. An underpressure is applied to all micropipettes via the pressure supply line 81, so that the carrier liquid is sucked into the carrier volume 25 of each of the micropipettes 20. The carrier liquid is introduced to a point where a fill level is reached at height H over the respective piezo element. The carrier liquid acts to convey a pressure pulse generated at the piezo elements to a working substance loaded in the micropipette tip in the loading volume 24 for the release of microdrops. This advantageously reduces the working substance volumes required in the sub-microliter range.

In a second step, the dispensing head 10 is moved to a microtiter plate 92 and lowered on the microtiter reservoirs 921, 922, 923, . . . in such a way that the micropipette tips become immersed in the reservoirs. By again applying an underpressure over the pressure supply line 81, the respective active substance in the micropipette tip is drawn into the load containing portion 24. Proper selection of carrier liquid and solvent for the working substance prevents both liquids from becoming mixed together.

The dispensing head 10 is subsequently moved to the reaction substrate 93, where the intended combinatory reaction is executed via the planned positioning of microdrops in the individual working substances at predetermined locations on the substrate 93.

The advantage to this procedure is that working substances are received at the dispensing head with the branching arrangement, which exhibits a very simple design, without having to actuate individual valves.

The dispensing head according to the invention is preferably used in processes involving biotechnology, genetic engineering or chemical technology. The described matrix with perpendicular, or oblique rows can also be replaced by another two-dimensional arrangement. If the micropipettes are arranged in a circle, for example, actuation does not take place via Cartesian x-y coordinates, but via polar coordinates. In this case, the demultiplexer circuits each execute a radius and angle selection.

The invention offers at least the following advantages. The multi-channel dispensing head according to the invention has a greatly simplified design, which also permits a simplification of micropipette actuation depending on the specific micropipette arrangement through the use of demultiplex technology. This relates both to the number of ground and signal lines leading to the dispensing head, which can be reduced to two lines regardless of the number of micropipettes, along with the scope of control electronics required for actuating the micropipettes. In addition, the simplified structure is easier to manipulate, and, hence, can be positioned more precisely. Finally, the arrangement of micropipettes on a shared carrier makes it possible to reduce the micropipette distance, so that working substances can be taken up by microtiter plates at a small distance between the individual microtiter volumes. The number of parallel processed substances increases, thereby resulting in a corresponding time savings. For the first time, the multi-channel dispensing head according to the invention enables the fully automatic and reproducible control of dispensing head positioning and microdrop release times based on predetermined program patterns, e.g., using a control computer.

What is claimed is:

1. A multi-channel dispensing head comprising: a plurality of micropipettes, each micropipette having an electrically actuatable trigger device with a ground and signal terminal; and a shared carrier having a plurality of receptacles located in a one- or two-dimensional arrangement and sized and shaped to receive said micropipettes, the shared carrier having a plurality of ground and a plurality of signal contacts, a ground and signal contact being located at each receptacle, wherein the plurality of ground and plurality of signal contacts on the carrier are spaced apart in the direction of a longitudinal axis extending respective micropipettes and each of the plurality of ground and plurality of signal contacts on the carrier contacting each of said ground and signal terminals of the trigger devices, respectively.

2. The multi-channel dispensing head according to claim 1, wherein the micropipettes form several straight or curved rows along a first dimension, and wherein the ground contacts of each row are electrically interconnected, and each of the signal contacts are connected with a first demultiplexer circuit.

3. The multi-channel dispensing head according to claim 2, in which the micropipettes form several columns along a second dimension, which columns run obliquely or substantially perpendicularly to the micropipette rows with connected ground contacts, wherein the ground contacts connected in rows are each contacted with a second demultiplexer circuit and individually actuatable with the latter, and wherein the signal contacts in the micropipette columns are each electrically interconnected and the signal contacts connected in columns are each connected with the first demultiplexer circuit.

4. The multi-channel dispensing head according to claim 1, in which the micropipettes are arranged as a matrix in mutually substantially perpendicular or oblique rows and columns, wherein the ground contacts are electrically connected in rows, and the signal contacts in columns, and wherein the shared ground contacts of each individual row and the shared signal contacts of each individual column are each connected with a first or second demultiplexer circuit.

5. The multi-channel dispensing head according to claim 1, in which the micropipettes are arranged as a matrix in mutually substantially perpendicular or oblique rows and columns, wherein the signal contacts of all micropipettes are electrically interconnected as a shared contact, and each ground contact of each micropipette is connected with a demultiplexer circuit via a separate ground line.

6. The multi-channel dispensing head according to claim 1, in which the micropipettes are arranged such that tips of the micropipettes form a pattern that corresponds to a pattern of reservoirs of a microtiter plate.

7. The multi-channel dispensing head according to claim 1, in which the ground and signal contacts are threaded necks or spring elements, which engage or project into the receptacles, and form attachment devices for the latter.

8. The multi-channel dispensing head according to claim 3, in which the demultiplexing circuits and a power supply unit are connected to the carrier and can move with the latter.

9. The multi-channel dispensing head according to claim 3, in which the demultiplexer circuits each exhibit one demultiplexer and one switching arrangement, wherein each switching arrangement contains numerous switching units, each corresponding to the number of rows with electrically connected ground contacts, and the rows with electrically connected signal contacts running obliquely or perpendicularly thereto.

10. The multi-channel dispensing head according to claim 1, in which the micropipettes each connect to a pressure line, and each pressure line is connected to a pressure supply line via a distributor secured to the dispensing head.

11. The multi-channel dispensing head according to claim 10, in which the distributor is multi-valved or is branched.

12. The multi-channel dispensing head according to claim 1, in which the electrically actuatable trigger device is a piezo element or a valve.

* * * * *